United States Patent [19]

Nakazawa et al.

[11] Patent Number: 5,955,627
[45] Date of Patent: Sep. 21, 1999

[54] PROCESS FOR THE PREPARATION OF CYCLOPROPYLACETYLENE DERIVATIVES

[75] Inventors: Makoto Nakazawa; Toshimichi Mitani; Yoichi Satake; Shigeo Oozono; Goro Asanuma; Manzo Shiono, all of Kurashiki, Japan

[73] Assignee: Kuraray Co., Ltd., Kurashiki, Japan

[21] Appl. No.: 08/989,412

[22] Filed: Dec. 12, 1997

[30] Foreign Application Priority Data

Dec. 16, 1996 [JP] Japan .................................... 8-335746
Mar. 19, 1997 [JP] Japan .................................... 9-065845
Oct. 22, 1997 [JP] Japan .................................... 9-290070

[51] Int. Cl.[6] .................... C07C 51/377; C07C 67/317
[52] U.S. Cl. .......................... 560/124; 562/506; 570/186
[58] Field of Search ............................ 562/506; 570/186; 560/124

[56] References Cited

FOREIGN PATENT DOCUMENTS

WO 96/22955   8/1996   WIPO.

OTHER PUBLICATIONS

Winfried Schoberth, et al., Synthesis, pp. 703, Dec. 1972, "Eine Einfache Herstellungsmethode fuer Cyclopropylacetylen".
J. Salaun, J. Org. Chem., vol. 41, No. 7, pp. 1237–1240, 1976, "Preparation and Substituent Effect in the Solvolysis of 1–Ethynylcyclopropyl Tosylates".
Andrew S. Thompson, et al., Tetrahedron Letters, vol. 36, No. 49. pp. 8937–8940, 1995, "Use of an Ephedrine Alkoxide to Mediate Enantioselective Addition of an Acetylide to a Prochiral Ketone: Asymmetric Synthesis of the Reverse Transcriptase Inhibitor L–743,726".
Edward Piers, et al., Tetrahedron, vol. 45, No. 2, pp. 363–380, 1989, "Reaction of (Trimethylstanny)Copper(I) Reagents with α,β–Acetylenic Esters. Stereocontrolled Synthesis of Alkyl (E)– and (Z)–3–Trimethylstannyl–2–Alkenoates".
Daniel Bertin, et al., Comptes Rendus, Academie des Sciences, vol. 229, p. 660–663, Oct. 3, 1949, "Chimie Organique—L'α–Naphtylacetylene".
Wilhelm Manchot, Justus Liebigs Annalen der Chemie, vol. 387, pp. 257, 281–283, 1912, "Zur Kenntnis der Koerper mit Dreifacher Bindung".
Zhenkun MA, et al., Tetrahedron: Asymmetry, vol. 8, No. 6, pp. 883–887, 1997, "Asymmetric Dipolar Cycloaddition Reactions: A Practical, Convergent Synthesis of Chiral Pyrrolidines".
Lee Irvin Smith, et al., Cyclopropyl Nitrocyclopropyl Ketones with Alkaline Reagents, Journal of the American Chemical Society, vol. 73, pp. 3831–3837, Aug. 1951, "Cyclopropanes. V.[1] Cyclopropyl Nitrocyclopropyl Ketones, and Their Behavior Toward Alkaline Reagents".
Susan C. Ward, et al., J. Org. Chem., vol. 59, No. 21, pp. 6476–6479, 1994, "[2 + 2] Photocycloaddition of Cinnamyloxy Silanes".
Russell C. Petter, et al., J. Org. Chem., vol. 55, No. 10, pp. 3088–3097, 1990, "Inhibition of γ–Butyrobetaine Hydroxylase by Cyclopropyl–Substituted γ–Butyrobetaines".

Margaret J. Jorgenson, Journal of the American Chemical Society, vol. 91, No. 23, pp. 6432–6443, Nov. 5, 1969, "Photochemistry of α,β–Unsaturated Esters. VII. The Photolytic Behavior of Vinylcyclopropanecarboxylates".
Margaret J. Jorgenson, et al, Journal of the American Chemical Society, vol. 90, No. 14, pp. 3769–3774, Jul. 3, 1968, "Cyclopropyl Conjugation in Olefinic Esters. Conformational Effects on Ultraviolet Absorption[1]".
J.P. Marino, et al., J. Org. Chem., vol. 41, No. 22, 1976, pp. 3629–3632, "A Regiospecific Synthesis of Functionalized Vinylcyclopropanes via Cyclopropyl Cuprates".
Warren J. Hehre, Journal of the American Chemical Society, vol. 94, No. 19, pp. 6592–6597, "Vinylcyclopropane and Vinylcyclobutane", Sep. 20, 1972.
Dennis P. Curran, et al., Tetrahedron, vol. 47, No. 32, pp. 6171–6188, "Iodine Atom Transfer Addition Reactions with Alkynes. Part 1: Alkyl Iodides", 1991.

Primary Examiner—Richard L. Raymond
Attorney, Agent, or Firm—Oblon, Spivak, McClelland, Maier & Neustadt, P.C.

[57]   ABSTRACT

According to the present invention, a process for the preparation of a cyclopropylacetylene derivative represented by the following formula (III):

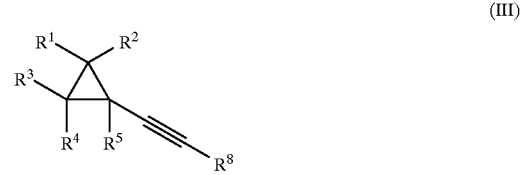

(III)

is provided, which comprises reacting a cyclopropylacrylic acid derivative represented by the following formula (I):

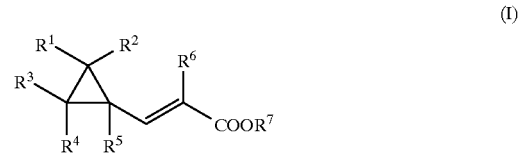

(I)

with a halogenating agent to obtain a halogenocyclopropylpropionic acid derivative represented by the following formula (II):

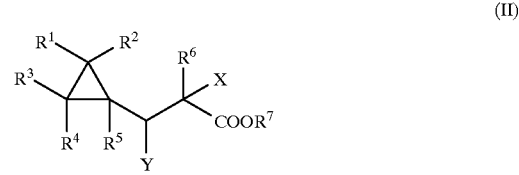

(II)

and reacting the halogenocyclopropylpropionic acid derivative with a base.

14 Claims, No Drawings

PROCESS FOR THE PREPARATION OF CYCLOPROPYLACETYLENE DERIVATIVES

BACKGROUND OF THE INVENTION

1. Field of the Invention

The present invention relates to process for the preparation of a cyclopropylacetylene derivative and a cyclopropylacrylic acid derivative which is an intermediate in synthesis of the cyclopropylacetylene derivative. A cyclopropylacetylene derivative produced by the present invention is useful as an intermediate in synthesis for a compound having a cyclopropane skeleton, for example a benzoxazinone derivative (L-743726), which has an anti-HIV activity (Tetrahedron Letters, vol. 36, p. 8937 (1995)) and the like.

2. Discussion of the Related Art

Recently, many physiologically active substances having a cyclopropane skeleton have been discovered. Well known methods of producing a cyclopropylacetylene derivative, for example cyclopropylacetylene, which is useful for an intermediate in synthesis for these compounds, are:

(1) a method in which cyclopropyl methyl ketone is reacted with phosphorus pentachloride in carbon tetrachloride to produce 1,1-dichloro-1-cyclopropylethane, which is dehydrochlorinated by potassium tert-butoxide (Synthesis, p. 703, (1972) and Journal of Organic Chemistry, vol. 41, p. 1237 (1976));

(2) a method in which 5-chloropentyne is reacted with n-butyl lithium in cyclohexane (Tetrahedron Letters, vol. 36, p. 8937 (1995)); and (3) a method in which cyclopropanecarboxaldehyde is reacted with carbon tetrabromide in the presence of triphenylphosphine by Wittig reaction to produce 1,1-dibromo-2-cyclopropylethylene, followed by the reaction with methyllithium (Tetrahedron, vol. 45, p. 363 (1989)).

However, the method (1) affords many by-products and a yield of the target compound is low, the method (2) requires use of expensive n-butyl lithium or lithium diisopropylamide and the method (3) produces large amount of triphenylphosphine oxide as a by-product which is troublesome to separate. Therefore, these methods are hard to evaluate as being industrially useful methods for cyclopropylacetylene.

On the other hand, as methods to construct a cyclopropane skeleton, known are: a Simmons-Smith method in which olef in is reacted with carbene that is produced by the reaction of 1,1-dihalo-compound and zinc copper alloy (New Experimental Chemistry Lecture Course, vol. 14, p. 84 (1977)); a method in which sulfur ylid is reacted with olefin (New Experimental Chemistry Lecture Course, vol. 14, p. 91 (1977)); a method using a decomposition reaction of an azo compound (New Experimental Chemistry Lecture Course, vol. 14, p. 82 (1977)); and an intramolecular cyclization reaction of a butanoic acid derivative having a leaving group at γ-position (New Experimental Chemistry Lecture Course, vol. 14, p. 93 (1977)).

As methods to construct an acetylene structure, known are: a coupling reaction of a metal acetylide (a metallic salt of acetylene) with a compound having a leaving group (New Experimental Chemistry Lecture Course, vol. 14, p. 271 (1977)); a reaction of a halogeno compound with a base (The fourth edition: Experimental Chemistry Lecture Course, vol. 19, p. 298 (1992)); a reaction of a nitrogen-containing compound such as hydrazone with a mercury compound or a base (The fourth edition: Experimental Chemistry Lecture Course, vol. 19, p. 310 (1992)); and an isomerization of an acetylene compound by a base (The fourth edition: Experimental Chemistry Lecture Course, vol. 19, p. 312 (1992)).

However, if a method mentioned above to construct a cyclopropane skeleton is applied to synthesis of a cyclopropylacetylene derivative, there arise problems that a side-reaction between carbene and acetylene occurs and many stages in a process are required in construction of a acetylene structure.

In addition to the above mentioned methods, it is known that an aldehyde derivative having a naphthalene ring is transformed by way of an acrylic acid derivative, to a vinyl derivative and to an acetylene derivative (Comptes Rendus, vol. 229, p. 660 (1949) and Justus Liebigs Annalen der Chemie, vol. 387, p.257 (1912)). But a cyclopropane ring has a high distortion, at which point the ring is different from a naphtalene ring, to cause a ring-opening reaction by electrophile (Journal of Synthetic Organic Chemistry, Japan, vol. 41, p. 22 (1983)). Therefore, it is thought that if such a method is applied to synthesis of a cyclopropylacetylene derivative, a side reaction which is represented by a ring-opening of a cyclopropane ring by bromine has a high probability to occur (Angewandte Chemie International Edition in English, vol. 15, p. 762 (1976)).

As a method of production of a cyclopropylacrylic acid derivative, known are the following methods: (4) a method in which cyclopropanecarboxaldehyde is reacted with malonic acid using pyridine as a solvent and a base (Tetrahedron: Asymmetry, vol. 8, p. 883 (1997) and Journal of the American Chemical Society, vol. 73, p. 3831 (1951)); (5) a method in which cyclopropanecarboxaldehyde is reacted with phosphonic acid derivative in the presence of a base to synthesize cyclopropylacrylate ester (Journal of Organic Chemistry, vol. 59, p. 6476 (1994), Journal of Organic Chemistry, vol. 55, p. 3088 (1990), Journal of the American Chemical Society, vol. 91, p. 6432 (1969) and Journal of the American Chemical Society, vol. 90, p. 3769 (1968)); and (6) an addition reaction of an acetylenecarboxylate with dicyclopropyl copper derivative prepared from cyclopropyl halide (Journal of Organic Chemistry, vol. 41, p. 3629 (1976)).

However, it is difficult that these methods are applied to an industrial production of a cyclopropylacrylic acid derivative by following reasons; according to the method (4), since pyridine is used as a solvent, removal and recovery of pyridine are problematic in an industrial scale of synthesis and moreover, a reaction requires a long time of period; according to the method (5), it is necessary to use expensive n-butyllithium or sodium hydride; and according to the method (6), it is necessary to employ many stages in synthesis of a starting material.

Under such circumstances, desired is a method in which a cyclopropylacetylene derivative and a cyclopropylacrylic acid derivative, which is an intermediate in synthesis of the cyclopropylacetylene derivative, can be produced in good yields under moderate conditions and thereby advantageously on an industrial scale.

SUMMARY OF THE INVENTION

A first object of the present invention is to provide a method in which a cyclopropylacetylene derivative and a cyclopropylacrylic acid derivative, which is an intermediate in synthesis of-the cyclopropylacetylene derivative, can be produced in good yields under moderate conditions and thereby advantageously on an industrial scale.

A second object of the present invention is to provide a new intermediate, which is useful in the production of cyclopropylacetylene derivative.

That is, a first embodiment of the present invention provides a process for the preparation of a cyclopropylacetylene derivative represented by the following formula (III):

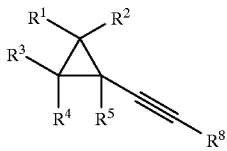
(III)

wherein $R^1$, $R^2$, $R^3$, $R^4$ and $R^5$ each represents a hydrogen atom or an alkyl group which may have a substituent, and $R^8$ represents a hydrogen atom, an alkyl group which may have a substituent, a carboxyl group or a protected carboxyl group (hereinafter simply referred to as cyclopropylacetylene derivative (III)), which comprises reacting a cyclopropylacrylic acid derivative represented by the following formula (I):

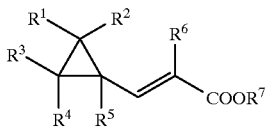
(I)

wherein $R^1$, $R^2$, $R^3$, $R^4$ and $R^5$ have the same meanings as defined above, $R^6$ represents a hydrogen atom, an alkyl group which may have a substituent, a carboxyl group or a protected carboxyl group, and $R^7$ represents a hydrogen atom or a protecting group for a carboxyl group (hereinafter simply referred to as cyclopropylacrylic acid derivative (I)), with a halogenating agent to obtain a halogenocyclopropylpropionic acid derivative represented by the following formula (II):

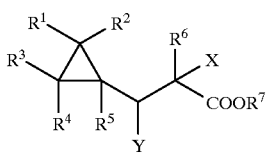
(II)

wherein $R^1$, $R^2$, $R^3$, $R^4$, $R^5$, $R^6$ and $R^7$ have the same meanings as defined above, and X and Y each represents a halogen atom (hereinafter simply referred to as halogenocyclopropylpropionic acid derivative (II)), and reacting the halogenocyclopropylpropionic acid derivative (II) with a base.

A second embodiment of the present invention provides a process for the preparation of a cyclopropylacetylene derivative (III), which comprises reacting a halogenocyclopropylpropionic acid derivative (II) with a base.

A third embodiment of the present invention provide a process for the preparation of a cyclopropylacetylene derivative (III), which comprises reacting a halogenocyclopropylpropionic acid derivative (II) with a base to obtain a cyclopropylvinyl derivative represented by the following formula (IV):

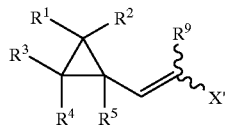
(IV)

wherein $R^1$, $R^2$, $R^3$, $R^4$, $R^5$ and X have the same meanings as defined above, and $R^9$ represents a hydrogen atom, an alkyl group which may have a substituent, a carboxyl group or a protected carboxyl group (hereinafter simply referred to as cyclopropylvinyl derivative (IV)), and reacting the cyclopropylvinyl derivative (IV) with a base.

A fourth embodiment of the present invention provides a process for the preparation of a cyclopropylacetylene derivative (III), which comprises reacting a cyclopropylvinyl derivative (IV) with a base.

A fifth embodiment of the present invention provide a process for the preparation of a cyclopropylvinyl derivative (IV), which comprises reacting a halogenocyclopropylpropionic acid derivative (II) with a base.

A sixth embodiment of the present invention provides a process for the preparation of a cyclopropylvinyl derivative (IV), which comprises reacting a cyclopropylacrylic acid derivative (I) with a halogenating agent and a base.

A seventh embodiment of the present invention provides a cyclopropylvinyl derivative represented by the following formula (IV-1):

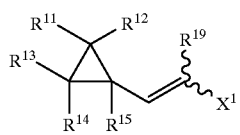
(IV-1)

wherein $R^{11}$, $R^{12}$, $R^{13}$, $R^{14}$ and $R^{15}$ each represents a hydrogen atom or an alkyl group which may be substituted with a hydroxyl group, an alkoxyl group or an aryl group, $R^{19}$ represents a hydrogen atom, an alkyl group which may have a substituent, a carboxyl group or a protected carboxyl group, and $X^1$ represents a halogen atom.

A eighth embodiment of the present invention provides a halogenocyclopropylpropionic acid derivative (II).

A ninth embodiment of the present invention provides a process for the preparation of a halogenocyclopropylpropionic acid derivative (II), which comprises reacting a cyclopropylacrylic acid derivative (I) with a halogenating agent.

A tenth embodiment of the present invention provides a process for the preparation of a cyclopropylacrylic acid derivative (I), which comprises reacting a cyclopropanecarboxaldehyde derivative represented by the following formula (V):

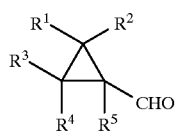
(V)

wherein $R^1$, $R^2$, $R^3$, $R^4$ and $R^5$ have the same meanings as defined above (hereinafter simply referred to as cyclopropanecarboxaldehyde derivative (V)), with an ester in the presence of a base.

An eleventh embodiment of the present invention provides a process for the preparation of a cyclopropylacrylic acid derivative (I), which comprises reacting a cyclopropanecarboxaldehyde derivative (V) with an ester in the presence of a base to obtain a cyclopropylpropionic acid derivative represented by the following formula (VI):

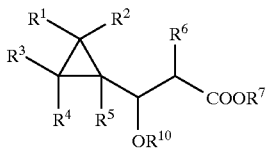

wherein $R^1$, $R^2$, $R^3$, $R^4$, $R^5$, $R^6$ and $R^7$ have the same meanings as defined above, and $R^{10}$ represents a hydrogen atom or an alkyl group which may have a substituent (hereinafter simply referred to as cyclopropylpropionic acid derivative (VI)), and subjecting the cyclopropylpropionic acid derivative (VI) to an elimination reaction in the presence of a base.

A twelfth embodiment of the present invention provides a cyclopropylpropionic acid derivative represented by the following formula (VI-I):

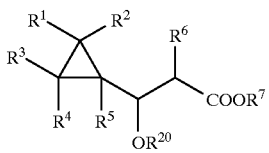

wherein $R^1$, $R^2$, $R^3$, $R^4$, $R^5$, $R^6$ and $R^7$ have the same meanings as defined above, and $R^{20}$ represents an alkyl group which may have a substituent.

A thirteenth embodiment of the present invention provides a process for the preparation of cyclopropylacrylic acid derivative represented by the following formula (I-1):

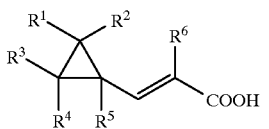

wherein $R^1$, $R^2$, $R^3$, $R^4$, $R^5$ and $R^6$ have the same meanings as defined above (hereinafter simply referred to as cyclopropylacrylic acid derivative (I-1)), which comprises reacting a cyclopropanecarboxaldehyde derivative (V) with malonic acid in the presence of a base while a produced water is removed outside the reaction system.

DETAILED DESCRIPTION OF THE INVENTION

Examples of the alkyl groups represented by $R^1$, $R^2$, $R^3$, $R^4$, $R^5$, $R^6$, $R^8$, $R^9$, $R^{10}$, $R^{19}$ and $R^{20}$ in the above formulae include methyl, ethyl, propyl, isopropyl, butyl, isobutyl, tert-butyl or the like.

These alkyl groups each may have a substituent and examples of such substituents include hydroxyl group; alkoxyl groups such as methoxy, ethoxy, propoxy and butoxy or the like; tri-substituted silyloxy groups such as tert-butyldimethylsilyloxy, tert-butyldiphenylsilyloxy or the like; and aryl groups such as phenyl, p-methoxyphenyl or the like.

In the case where $R^6$, $R^8$, $R^9$ and $R^{19}$ each represents a protected carboxyl group, the protecting group for a carboxyl group may be any commonly known protecting group. Examples of these protecting groups include alkyl groups such as methyl, ethyl, propyl, isopropyl, butyl, isobutyl, tert-butyl or the like; and aralkyl groups such as benzyl, p-methoxybenzyl group or the like. These alkyl groups and aralkyl groups each may have a substituent and examples of such substituents include alkoxyl groups such as methoxy, ethoxy, propoxy, butoxy or the like.

In the case where $R^7$ represents a protecting group of carboxyl group, the protecting group may be any commonly known protecting group. Examples of these protecting groups include alkyl groups such as methyl, ethyl, propyl, isopropyl, butyl, isobutyl, tert-butyl or the like; and aralkyl groups such as benzyl, p-methoxybenzyl group or the like. These alkyl groups and aralkyl groups each may have a substituent and examples of such substituents include alkoxyl groups such as methoxy, ethoxy, propoxy, butoxy or the like.

Examples of the alkyl groups represented by $R^{11}$, $R^{12}$, $R^{13}$, $R^{14}$ and $R^{15}$ include methyl, ethyl, propyl, isopropyl, butyl, isobutyl, tert-butyl or the like.

These alkyl groups each may have a substituent and examples of such substituents include hydroxyl group; alkoxyl groups such as methoxy, ethoxy, propoxy, butoxy or the like; and aryl groups such as phenyl, p-methoxyphenyl or the like.

Examples of the halogen atoms represented by X, Y and $X^1$ include fluorine atom, chlorine atom, bromine atom and iodine atom, and bromine atom is preferably used.

A production method of the present invention will be described about each step in detail.

Step 1: A Step of Producing a Cyclopropylacrylic Acid Derivative (I) from a Cyclopropanecarboxaldehyde Derivative (V)

Step 1-1:

First of all, a step of reacting a cyclopropanecarboxaldehyde derivative (V) with an ester in the presence of a base will be described.

As an ester, any ester which has a hydrogen atom at an α-position of a carbonyl group may be used. Examples of the esters include acetates such as methyl acetate, ethyl acetate, n-propyl acetate, isopropyl acetate, n-butyl acetate, isobutyl acetate, tert-butyl acetate, phenyl acetate, benzyl acetate or the like; propionates such as methyl propionate, ethyl propionate, n-propyl propionate, isopropyl propionate, n-butyl propionate, isobutyl propionate, tert-butyl propionate, phenyl propionate, benzyl propionate or the like; butanoates such as methyl butanoate, ethyl butanoate, n-propyl butanoate, isopropyl butanoate, n-butyl butanoate, isobutyl butanoate, tert-butyl butanoate, phenyl butanoate, benzyl butanoate or the like; pentanoates such as methyl pentanoate, ethyl pentanoate, n-propyl pentanoate, isopropyl pentanoate, n-butyl pentanoate, isobutyl pentanoate, tert-butyl pentanoate, phenyl pentanoate, benzyl pentanoate or the like; and malonates such as monomethyl malonate, dimethyl malonate, monoethyl malonate, diethyl malonate, mono-n-propyl malonate, di-n-propyl malonate, mono-isopropyl malonate, diisopropyl malonate, mono-n-butyl malonate, di-n-butyl malonate, mono-isobutyl malonate, diisobutyl malonate, mono-tert-butyl malonate or the like. Among them, acetates and malonates are preferably used.

Amount of an ester is preferably in the range of 1 equivalent to 200 equivalents of a cyclopropanecarboxaldehyde derivative (V) and it is more preferably in the range of 1 equivalent to 10 equivalents.

A reaction in the step is conducted in the presence of a base. Examples of the bases include amines such as pyridine, triethylamine or the like; carbonates such as potassium carbonate, sodium carbonate or the like; metal hydroxides such as sodium hydroxide, potassium hydroxide or the like; and metal alkoxides such as sodium methoxide, potassium methoxide, sodium ethoxide, potassium ethoxide, sodium tert-butoxide, potassium tert-butoxide or the like. Amount of a base is preferably in the range of 1 equivalent to 100 equivalents of a cyclopropanecarboxaldehyde derivative (V).

A reaction may be conducted in any solvent as far as it gives no adverse influence on the reaction. Examples of the solvents include hydrocarbons such as pentane, hexane, heptane, octane, petroleum ether, benzene, toluene, xylene or the like; ethers such as diethyl ether, diisopropyl ether, tert-butylmethyl ether, anisole, tetrahydrofuran, dioxane, ethyleneglycol dimethyl ether, triethyleneglycol dimethyl ether or the like; halogenated hydrocarbons such as methylene chloride, chloroform, carbon tetrachloride, dichloroethane, trichloroethane, bromopropane, chlorobenzene, dichlorobenzene or the like; acetates such as methyl acetate, ethyl acetate, n-propyl acetate, isopropyl acetate, n-butyl acetate, isobutyl acetate, tert-butyl acetate or the like; alcohols such as methanol, ethanol, n-propanol, isopropanol, n-butanol, isobutanol, sec-butanol, tert-butanol, 1-pentanol, 2-pentanol, 3-pentanol, 2-methyl-1-butanol, 3-methyl-1-butanol, 3-methyl-2-butanol, 2-methyl-2-butanol, cyclohexanol, ethylene glycol, trimethylene glycol or the like; water; dimethyl sulfoxide; or a mixture solvent thereof. Any of the above mentioned bases which are in a liquid state may be used as a solvent. Generally, amount of a solvent is preferably in the range of 1 to 200 times as much as a weight of a cyclopropanecarboxaldehyde derivative (V).

A reaction is conducted by adding an ester and a base or a solution thereof to a cyclopropanecarboxaldehyde derivative (V) or its solution, or the cyclopropanecarboxaldehyde derivative (V) or its solution to the ester and the base or the solution thereof. A temperature of the reaction is preferably in the range of −100° C. to 200° C., or more preferably in the range of −20° C. to the boiling point of a solvent used.

A cyclopropanecarboxaldehyde derivative (V) is reacted with an ester in the presence of a base and thereby a cyclopropylpropionic acid derivative (VI) and a cyclopropylacrylic acid derivative (I) are obtained.

Thus obtained cyclopropylacrylic acid derivative (I) can be isolated and purified in a common method which is used for isolation and purification. For example, a reaction mixture is poured into a saline solution or water, and subjected to extraction with an organic solvent such as diethyl ether, ethyl acetate, methylene chloride or the like. If necessary, an extract is washed with a dilute hydrochloric acid solution, water, a saline solution or the like in order to remove a basic substance and a water soluble substance, the extract is further dried with anhydrous magnesium sulfate, anhydrous sodium sulfate or the like and thereafter the extract is further concentrated and the obtained crude product can be, if necessary, purified by distillation, chromatography, recrystallization or the like. If necessary, a protecting group of a cyclopropylacrylic acid derivative (I) may be deblocked. Without an after-treatment, a reaction solution may be provided for next reaction.

A cyclopropylpropionic acid derivative (VI) can also be isolated and purified in a common method which is used for isolation and purification. For example, a reaction mixture is poured into a saline solution or water, and subjected to extraction with an organic solvent such as diethyl ether, ethyl acetate, methylene chloride or the like. If necessary, an extract is washed with a dilute hydrochloric acid solution, water, a saline solution or the like in order to remove a basic substance and a water soluble substance, thereafter the extract is further concentrated and the obtained crude product can be, if necessary, purified by distillation, chromatography, recrystallization or the like. Without an after-treatment, a reaction solution may be provided for next reaction.

Thus obtained cyclopropylpropionic acid derivative (VI) can be subjected to an elimination reaction in the presence of a base so as to be transformed to a cyclopropylacrylic acid derivative (I).

Examples of the bases used here includes amines such as pyridine, triethylamine or the like; carbonates such as potassium carbonate, sodium carbonate or the like; metal hydroxides such as sodium hydroxide, potassium hydroxide or the like; and metal alkoxides such as sodium methoxide, potassium methoxide, sodium ethoxide, potassium ethoxide, sodium tert-butoxide, potassium tert-butoxide or the like. Amount of a base is preferably in the range of 0.01 equivalent to 100 equivalents of a cyclopropylpropionic acid derivative (VI).

A reaction may be conducted in any solvent as far as it gives no adverse influence on the reaction. Examples of the solvents include hydrocarbons such as pentane, hexane, heptane, octane, petroleum ether, benzene, toluene, xylene or the like; ethers such as diethyl ether, diisopropyl ether, tert-butylmethyl ether, anisole, tetrahydrofuran, dioxane, ethyleneglycol dimethyl ether, triethyleneglycol dimethyl ether or the like; halogenated hydrocarbons such as methylene chloride, chloroform, carbon tetrachloride, dichloroethane, trichloroethane, bromopropane, chlorobenzene, dichlorobenzene or the like; acetates such as methyl acetate, ethyl acetate, n-propyl acetate, isopropyl acetate, n-butyl acetate, isobutyl acetate, tert-butyl acetate or the like; dimethyl sulfoxide; or a mixture solvent thereof. Any of the above mentioned bases which are in a liquid state may be used as a solvent. Generally, amount of a solvent is preferably in the range of 1 to 200 times as much as a weight of a cyclopropylpropionic acid derivative (VI).

A reaction is conducted by adding a base or its solution to a cyclopropylpropionic acid derivative (VI) or its solution, or the cyclopropylpropionic acid derivative (VI) or its solution to the base or its solution. A temperature of the reaction is preferably in the range of −200° C. to 100° C., or more preferably in the range of −20° C. to the boiling point of a solvent used. Water or alcohol produced in the reaction may be removed outside the reaction system using means such as azeotropic distillation or the like.

Thus obtained cyclopropylacrylic acid derivative (I) can be subjected to the above mentioned isolation and purification.

Step 1-2:

Next, a step of reacting a cyclopropanecarboxaldehyde derivative (V) with malonic acid in the presence of a base to obtain a cyclopropylacrylic acid derivative (I-1) will be described.

In a process, the reaction is conducted by removing water, which is produced by the reaction, to outside of the system. A method to remove the produced water to outside of the system is not specially restrictive and, for example, a solid dehydrating agent such as silica gel, molecular sieve, anhydrous sodium sulfate or the like can be used. From a view point of an industrial practice, a simpler method is removal of water by azeotropic distillation using an organic solvent.

An organic solvent used here may be used as far as it does not give an adverse effect to a reaction of the present invention and gives azeotropic mixture with water. Examples of the solvents include ethers such as diethyl ether, diisopropyl ether or the like; hydrocarbons such as pentane, hexane, heptane, decane, cyclohexane, benzene, toluene, xylene or the like; halogenated hydrocarbons such as methylene chloride, 1,2-dichloroethane, chloroform or the like; esters such as ethyl acetate, propyl acetate, isopropyl acetate, butyl acetate or the like. Amount of a solvent, which is necessary for removal of water by azeotropic distillation, is preferably in the range of 0.2 to 20 times as much as a weight of malonic acid.

Examples of the bases used here include organic bases such as pyridine, triethylamine, piperidine, pyrrolidine or the like, and among them pyridine is preferable. Amount of a base is preferably in the range of 0.1 equivalent to 10 equivalents of a malonic acid and it is more preferably in the range of 0.5 equivalent to 2.0 equivalents from a view point of a reaction and economy.

In order to accelerate the reaction, it is preferable to conduct the reaction with an addition of a salt such as ammonium acetate as a catalyst. Amount of a catalyst is preferably in the range of 0.001 equivalent to 1.0 equivalent of a malonic acid.

In order to conduct the reaction in a reflux condition, a temperature of the reaction can commonly be in the range of 0° C. to 150° C., which depends on a kind and amount of an organic solvent used in the reaction. Though as a temperature is higher, a speed of the reaction is inclined to be faster, it is preferable to adopt a temperature in the range of 40° C. to 135° C., since a thermal decomposition occurs with ease at higher temperature. While the reaction is usually conducted under atmospheric pressure, there arises no problem if it is done under reduced or increased pressure.

Thus obtained cyclopropylacrylic acid derivative (I-1) is a compound categorically included in a cyclopropylacrylic acid derivative (I).

Step 2: A Step of Producing a Halogenocyclopropylpropionic Acid Derivative (II) by Reacting a Cyclopropylacrylic Acid Derivative (I) with a Halogenating Agent.

A halogenating agent may be any compound as far as it is constructed with a halogen atom. Examples of the halogenating agents include fluorine, chlorine, bromine, iodine or a mixture thereof. Amount of a halogenating agent is preferably 0.9 mol or more per mole of a cyclopropylacrylic acid derivative (I).

The reaction is generally conducted in any solvent, which gives no adverse influence on the reaction. Examples of the solvents include hydrocarbons such as pentane, hexane, heptane, octane, petroleum ether, benzene, toluene, xylene or the like; ethers such as diethyl ether, diisopropyl ether, tert-butylmethyl ether, anisole, tetrahydrofuran, dioxane, ethyleneglycol dimethyl ether, triethyleneglycol dimethyl ether or the like; halogenated hydrocarbons such as methylene chloride, chloroform, carbon tetrachloride, dichloroethane, trichloroethane, bromopropane, chlorobenzene, dichlorobenzene or the like; acetates such as methyl acetate, ethyl acetate, n-propyl acetate, isopropyl acetate, n-butyl acetate, isobutyl acetate, tert-butyl acetate or the like; alcohols such as methanol, ethanol, n-propanol, isopropanol, n-butanol, isobutanol, sec-butanol, tert-butanol, 1-pentanol, 2-pentanol, 3-pentanol, 2-methyl-1-butanol, 3-methy-1-butanol, 3-methyl-2-butanol, 2-metyl-2-butanol, cyclohexanol, ethylene glycol, trimethylene glycol or the like; cyanohydrocarbons such as acetonitrile, propionitrile, butyronitrile, benzonitrile or the like; water; dimethyl sulfoxide; or a mixture solvent thereof. Generally, amount of a solvent is preferably in the range of 1 to 200 times as much as a weight of a cyclopropylacrylic acid derivative (I).

The reaction is conducted by adding a halogenating agent or its solution to a cyclopropylacrylic acid derivative (I) or its solution, or the cyclopropylacrylic acid derivative (I) or its solution to the halogenating agent or its solution. A temperature of the reaction is preferably in the range of −100° C. to 100° C., or more preferably in the range of −20° C. to 40° C.

Thus obtained halogenocyclopropylpropionic acid derivative (II) can be isolated and purified in a common method which is used for isolation and purification. For example, a reaction mixture is poured into a saline solution or water, and subjected to extraction with an organic solvent such as diethyl ether, ethyl acetate, methylene chloride or the like. If necessary, an extract is washed with a dilute hydrochloric acid solution, water, a salt solution or the like in order to remove a water soluble substance, thereafter the extract is further concentrated and the obtained crude product can be, if necessary, purified by distillation, chromatography, recrystallization or the like. Without an after-treatment, a reaction solution may be provided for next reaction.

Step 3: A Step of Producing a Cyclopropylacetylene Derivative (III) by Reacting a Halogenocyclopropylpropionic Acid Derivative (II) with a Base Via a Cyclopropylvinyl Derivative (IV) as an Intermediate.

Examples of the bases include amines such as pyridine, triethylamine or the like; carbonates such as potassium carbonate, sodium carbonate or the like; metal hydroxides such as sodium hydroxide, potassium hydroxide or the like; metal alkoxides such as sodium methoxide, potassium methoxide, sodium ethoxide, potassium ethoxide, sodium tert-butoxide, potassium tert-butoxide or the like; alkylmetal compounds such as methyllithium, ethyllithium, propyllithium, butyllithium or the like; and arylmetal compounds such as phenyllithium or the like. Amount of a base is preferably in the range of 1 equivalent to 100 equivalents of a halogenocyclopropylpropionic acid derivative (II).

The reaction is generally conducted in any solvent, which gives no adverse influence on the reaction. Examples of the solvents include hydrocarbons such as pentane, hexane, heptane, octane, petroleum ether, benzene, toluene, xylene or the like; ethers such as diethyl ether, diisopropyl ether, tert-butylmethyl ether, anisole, tetrahydrofuran, dioxane, ethyleneglycol dimethyl ether, triethyleneglycol dimethyl ether or the like; halogenated hydrocarbons such as methylene chloride, chloroform, carbon tetrachloride, dichloroethane, trichloroethane, bromopropane, chlorobenzene, dichlorobenzene or the like; acetates such as methyl acetate, ethyl acetate, n-propyl acetate, isopropyl acetate, n-butyl acetate, isobutyl acetate, tert-butyl acetate or the like; alcohols such as methanol, ethanol, n-propanol, isopropanol, n-butanol, isobutanol, sec-butanol, tert-butanol, 1-pentanol, 2-pentanol, 3-pentanol, 2-methyl-1-butanol, 3-methy-1-butanol, 3-methyl-2-butanol, 2-methyl-2-butanol, cyclohexanol, ethylene glycol, trimethylene glycol or the like; cyanohydrocarbons such as acetonitrile, propionitrile, butyronitrile, benzonitrile or the like; water; dimetyl sulfoxide; or a mixture solvent thereof. Generally, amount of a solvent is preferably in the range of 1 to 200 times as much as a weight of a halogenocyclopropylpropionic acid derivative (II).

The reaction is conducted by adding a base or its solution to a halogenocyclopropylpropionic acid derivative (II) or its solution, or the halogenocyclopropylpropionic acid derivative (II) or its solution to the base or its solution. A temperature of the reaction is preferably in the range of −100° C. to 200° C., or more preferably in the range of −20° C. to 100° C.

A cyclopropylvinyl derivative (IV) or a cyclopropylacetylene derivative (III) is obtained by reacting a halogenocyclopropylpropionic acid derivative (II) with abase. The reaction can be advanced to a cyclopropylacetylene derivative (III) produced in one portion that amount of a base is in the range of 2 equivalents or more of a halogenocyclopropylpropionic acid derivative (II). Examples of such bases include metal hydroxides such as sodium hydroxide, potassium hydroxide or the like; metal alkoxides such as sodium methoxide, potassium methoxide, sodium ethoxide, potassium ethoxide, sodium tert-butoxide, potassium tert-butoxide or the like; alkylmetal compounds such as methyllithium, ethyllithium, propyllithium, butyllithium or the like; and arylmetal compounds such as phenyllithium or the like.

Thus obtained cyclopropylacetylene derivative (III) can be isolated and purified in a common method which is used for isolation and purification. For example, a reaction mixture is poured into a saline solution or water, and subjected to extraction with an organic solvent such as diethyl ether, ethyl acetate, methylene chloride or the like. If necessary, an extract is washed with a dilute hydrochloric acid solution, water, a saline solution or the like in order to remove a basic substance and a water soluble substance, thereafter the extract is further concentrated and the obtained crude product can be, if necessary, purified by distillation, chromatography, recrystallization or the like. Without an after-treatment, a reaction solution may be subjected to distillation, chromatography, recrystallization or the like as it is in order to isolate the product, depending on a requirement.

The reaction can be advanced to a cyclopropylvinyl derivative (IV) produced that amount of a base is in the range of 1 equivalent to 2 equivalents of a halogenocyclopropylpropionic acid derivative (II). Examples of such bases include amines such as pyridine, triethylamine or the like; carbonates such as potassium carbonate, sodium carbonate or the like; metal hydroxides such as sodium hydroxide, potassium hydroxide or the like; metal alkoxides such as sodium methoxide, potassium methoxide, sodium ethoxide, potassium ethoxide, sodium tert-butoxide, potassium tert-butoxide or the like; alkylmetal compounds such as methyllithium, ethyllithium, propyllithium, butyllithium or the like; and arylmetal compounds such as phenyllithium or the like.

Thus obtained cyclopropylvinyl derivative (IV) can be isolated and purified in a common method which is used for isolation and purification. For example, a reaction mixture is poured into a saline solution or water, and subjected to extraction with an organic solvent such as diethyl ether, ethyl acetate, methylene chloride or the like. If necessary, an extract is washed with a dilute hydrochloric acid solution, water, a saline solution or the like in order to remove a basic substance and a water soluble substance, thereafter the extract is further concentrated and the obtained crude product can be, if necessary, purified by distillation, chromatography, recrystallization or the like. Without an after-treatment, a reaction solution may be provided for next reaction.

Thus obtained cyclopropylvinyl derivative (IV) is reacted with a base and thereby can be transformed to a cyclopropylacetylene derivative (III).

Examples of the bases used here include metal hydroxides such as sodium hydroxide, potassium hydroxide or the like; metal alkoxides such as sodium methoxide, potassium methoxide, sodium ethoxide, potassium ethoxide, sodium tert-butoxide, potassium tert-butoxide or the like; alkylmetal compounds such as methyllithium, ethyllithium, propyllithium, butyllithium or the like; and arylmetal compounds such as phenyllithium or the like. Amount of a base is preferably in the range of 1 equivalent to 100 equivalents of a cyclopropylvinyl derivative (IV).

The reaction is generally conducted in any solvent, which gives no adverse influence on the reaction. Examples of the solvents include hydrocarbons such as pentane, hexane, heptane, octane, petroleum ether, benzene, toluene, xylene or the like; ethers such as diethyl ether, diisopropyl ether, tert-butylmethyl ether, anisole, tetrahydrofuran, dioxane, ethyleneglycol dimethyl ether, triethyleneglycol dimethyl ether or the like; alcohols such as methanol, ethanol, n-propanol, isopropanol, n-butanol, isobutanol, sec-butanol, tert-butanol, 1-pentanol, 2-pentanol, 3-pentanol, 2-methyl-1-butanol, 3-methyl-1-butanol, 3-methyl-2-butanol, 2-methyl-2-butanol, cyclohexanol, ethylene glycol, trimethylene glycol or the like; water; dimethyl sulfoxide; or a mixture solvent thereof. Generally, amount of a solvent is preferably in the range of 1 to 200 times as much as a weight of a cyclopropylvinyl derivative (IV).

The reaction is conducted by adding a base or its solution to a cyclopropylvinyl derivative (IV) or its solution, or the cyclopropylvinyl derivative (IV) or its solution to the base or its solution. A temperature of the reaction is preferably in the range of −20° C. to 250° C., or more preferably in the range of 0° C. to 200° C.

Thus obtained cyclopropylacetylene derivative (III) can be isolated and purified by the above mentioned methods.

In order to obtain a highly pure cyclopropylacetylene derivative (III), it is preferred that, purified cyclopropylvinyl derivative (IV) is used as a starting material.

A cyclopropylvinyl derivative (IV) can be obtained in one operation by reacting a cyclopropylacrylic acid derivative (I) with a halogenating agent and a base without isolation of a halogenocyclopropylpropionic acid derivative (II), wherein a halogenating agent and base similar to the above mentioned are used.

EXAMPLES

The present invention will hereinafter be described in further detail by examples and referential examples. It should however be borne in mind that the present invention will not be limited to or by the following examples.

Example 1

Synthesis of methyl cyclopropylacrylate and methyl 3-cyclopropyl-3-methoxypropionate To a solution of cyclopropanecarboxaldehyde (5 g) and methanol (0.2 ml) in methyl acetate (20.3 ml) was added a small portion of sodium metal (1.78 g) below 5° C. After the addition was complete, the reaction mixture was stirred for 8 hours below 20° C. After the reaction mixture being filtered, the filtrate was poured into 1N hydrochloric acid and extracted with methyl acetate. After the extraction was dried over anhydrous magnesium sulfate and filtered, the filtrate was concentrated to give a mixture of methyl (E)-cyclopropylacrylate and methyl 3-cyclopropyl-3-methoxypropionate (6.16 g), with the followed physical data.

Methyl (E)-cyclopropylacrylate:
$^1$H-NMR spectrum (270 MHz, CDCl$_3$, TMS, ppm) δ: 6.42(dd,J=10.4,15.8 Hz,1H), 5.90(d,J=15.8 Hz,1H), 3.71(s, 3H), 1.5–1.65(m,1H), 0.85–1.05(m,2H), 0.55–0.75(m,2H).
$^{13}$C-NMR spectrum (67, 5 MHz, CDCl3, TMS, ppm) δ: 167.28, 154.48, 117.75, 51.38, 14.48, 8.73(2).
Methyl 3-cyclopropyl-3-methoxypropionate:
$^1$H-NMR spectrum (270 MHz, CDCl$_3$, TMS, ppm) δ: 3.70(dd,J=9.2,15.6 Hz,1H), 3.43(s,3H), 2.9–3.1(m,1H), 2.63–2.74(dd,J=9.2,15.6 Hz,1H), 2.54–2.62(dd,J=6.4,15.6 Hz,1H), 0.8–1.0(m,2H), 0.4–0.55(m,2H), 0.05–0.15(m,1H).

Example 2
Synthesis of methyl cyclopropylacrylate and methyl 3-cyclopropyl-3-methoxypropionate
Sodium methoxide (3.2 g, 59 mmol, 1.2 eq based on the cyclopropanecarboxaldehyde) was added to methyl acetate (30 g, 405 mmol) at room temperature under nitrogen atmosphere. To the reaction mixture was added cyclopropanecarboxaldehyde (3.5 g, 50 mmol) dropwise at room temperature. After the addition was complete, the solution was stirred and heated under reflux for 7 hours. The reaction mixture was poured in to cooled water. The aqueous layer was separated from the quenched solution stood for a few minutes. The organic layer was concentrated under reduced pressure to give the mixture of methyl cyclopropylacrylate and methyl 3-cyclopropyl-3-methoxypropionate (5.79 g, methyl cyclopropylacrylate:methyl 3-cyclopropyl-3-methoxypropionate=73.5:26.5).

Example 3
Synthesis of methyl cyclopropylacrylate and methyl 3-cyclopropyl-3-methoxypropionate
28%-Sodium methoxide in methanol (11.4 g, 59 mmol, 1.2 eq based on the cyclopropanecarboxaldehyde) was added to methyl acetate (30 g, 405 mmol) under nitrogen atmosphere. To the reaction mixture was added cyclopropanecarboxaldehyde (3.5 g, 50 mmol) dropwise at room temperature. After the addition was complete, the solution was stirred and heated under reflux for 6 hours. The reaction mixture was poured in to cooled water. The aqueous layer was separated from the quenched solution stood for a few minutes. The organic layer was concentrated under reduced pressure to give the mixture of methyl cyclopropylacrylate and methyl 3-cyclopropyl-3-methoxypropionate (5.49 g, methyl cyclopropylacrylate:methyl 3-cyclopropyl-3-methoxypropionate=60:40).

Example 4
Synthesis of methyl cyclopropylacrylate and methyl 3-cyclopropyl-3-methoxypropionate
28%-Sodium methoxide in methanol (11.4 g, 59 mmol, 1.2 eq based on the cyclopropanecarboxaldehyde) was added to the mixture solution of methyl acetate (8.89 g, 120 mmol) and tetrahydrofuran (21.11 g) at room temperature under nitrogen atmosphere. To the reaction mixture was added cyclopropanecarboxaldehyde (3.5 g, 50 mmol) dropwise at room temperature. After the addition was complete, the solution was stirred and heated under reflux for 5 hours. The reaction mixture was poured into cooled water. The aqueous layer was separated from the quenched solution stood for a few minutes. The aqueous layer was reextracted with methyl acetate. The combined organic layer was concentrated under reduced pressure to give the mixture of methyl cyclopropylacrylate and methyl 3-cyclopropyl-3-methoxypropionate (4.91 g, methyl cyclopropylacrylate:methyl 3-cyclopropyl-3-methoxypropionate=62:38).

Example 5
Synthesis of methyl cyclopropylacrylate as main product
Sodium methoxide (0.464 kg, 8.59 mol, 1.19 eq based on the cyclopropanecarboxaldehyde) was added to ethyl acetate (4.278 kg, 48.6 mol) at 0±5° C. under nitrogen atmosphere. To the reaction mixture was added cyclopropanecarboxaldehyde (0.506 kg, 7.22 mol) dropwise at 0±5° C. After the addition was complete, the solution was stirred at 0±5° C. for 5 hours. The reaction mixture was poured into cooled water (2.137 kg). The aqueous layer was separated from the quenched solution stood for a few minutes. The organic layer was concentrated under reduced pressure to give the mixture of methyl cyclopropylacrylate, ethyl cyclopropylacrylate, methyl 3-cyclopropyl-3-methoxypropionate, ethyl 3-cyclopropyl-3-methoxypropionate, methyl 3-cyclopropyl-3-ethoxypropionate and ethyl 3-cyclopropyl-3-ethoxypropionate (928.48 g, methyl cyclopropylacrylate:ethyl cyclopropylacrylate methyl 3-cyclopropyl-3-methoxypropionate:ethyl 3-cyclopropyl-3-methoxypropionate:methyl 3-cyclopropyl-3-ethoxypropionate:ethyl 3-cyclopropyl-3-ethoxypropionate= 25:25:12.5:12.5:12.5:12.5) with the followed physical data.
Ethyl (E)-cyclopropylacrylate:
$^1$H-NMR spectrum (270 MHz, CDCl$_3$, TMS, ppm) δ: 6.42(dd,J=9.89,15.8 Hz,1H), 5.89(d,J=15.8 Hz,1H), 4.17(q, J=6.93 Hz,2H), 1.5–1.7(m,1H), 1.28(t,J=6.93 Hz,3H), 0.85–1.05(m,2H), 0.55–0.75(m,2H).
Ethyl 3-cyclopropyl-3-methoxypropionate:
GC-Mass spectrum:M$^+$=172
Methyl 3-cyclopropyl-3-ethoxypropionate:
GC-Mass spectrum:M$^+$=172
Ethyl 3-cyclopropyl-3-ethoxypropionate:
GC-Mass spectrum:M$^+$=186

Example 6
Synthesis of ethyl cyclopropylacrylate as main product
Sodium ethoxide (0.578 kg, 8.49 mol, 1.19 eq based on the cyclopropanecarboxaldehyde) was added to ethyl acetate (4.278 kg, 48.6 mol) at 0±5° C. under nitrogen atmosphere. To the reaction mixture was added cyclopropanecarboxaldehyde (0.500 kg, 7.13 mol) dropwise at 0±5° C. After the addition was complete, the solution was stirred at 70° C. for 6 hours. The reaction mixture was poured into cooled water (2.14 kg). The aqueous layer was separated from the quenched solution stood for a few minutes. The organic layer was concentrated under reduced pressure to give the mixture of ethyl cyclopropylacrylate and ethyl 3-cyclopropyl-3-ethoxypropionate (784.11 g, ethyl cyclopropylacrylate:ethyl 3-cyclopropyl-3-ethoxypropionate= 86:14).

Example 7
Synthesis of isopropyl cyclopropylacrylate as main product
Sodium methoxide (0.463 kg, 8.57 mol, 1.19 eq based on the cyclopropanecarboxaldehyde) was added to isopropyl acetate (4.278 kg, 41.9 mol) under nitrogen atmosphere. To the reaction mixture was added cyclopropanecarboxaldehyde (0.506 kg, 7.22 mol) dropwise at 0±5° C. After the addition was complete, the solution was stirred at 0±5° C. for 5 hours. The reaction mixture was poured into cooled water (2.137 kg). The aqueous layer was separated from the quenched solution stood for a few minutes. The organic layer was concentrated under reduced pressure to give the mixture of isopropyl cyclopropylacrylate as main product (1.049 kg, isopropyl cyclopropylacrylate:methyl cyclopropylacrylate:isopropyl 3-cyclopropyl-3-isopropoxypropionate:isopropyl 3-cyclopropyl-3- methoxypropionate:methyl 3-cyclopropyl-3-isopropoxypropionate:methyl 3-cyclopropyl-3-methoxypropionate=77.0:10.9:5.0:5.3:1.1:0.7) with the followed physical data.

Isopropyl (E)-cyclopropylacrylate:
$^1$H-NMR spectrum (270 MHz, CDCl$_3$, TMS, ppm) δ: 6.41(dd,J=9.71,15.9 Hz,1H), 5.88(d,J=15.9 Hz,1H), 5.04 (septet,J=5.29 Hz,1H), 1.45–1.65(m,1H), 1.24(d,J=5.29 Hz,6H), 0.8–1.0(m,2H), 0.55–0.7(m,2H).

Isopropyl 3-cyclopropyl-3-isopropoxypropionate:
GC-Mass spectrum:M$^+$=214

Isopropyl 3-cyclopropyl-3-methoxypropionate:
GC-Mass spectrum:M$^+$=186

Methyl 3-cyclopropyl-3-isopropoxypropionate:
GC-Mass spectrum:M$^+$=186

Example 8
Synthesis of methyl cyclopropylacrylate

To a solution of monomethyl malonate (14.16 g, 1.2 eq based on the cyclopropanecarboxaldehyde) and ammonium acetate (0.3 g) in benzene (20 ml) was added dropwise a solution of cyclopropanecarboxaldehyde (7.1 g, 101.3 mmol) in pyridine (11 ml) at 0±5° C. After addition, the solution was refluxed to remove water outside. To the reaction mixture was added 1N hydrochloric acid to acidify. After separation, the aqueous layer was extracted with diisopropyl ether (70 ml) twice. The combined organic layer was concentrated under reduced pressure to give methyl cyclopropylacrylate (11.1 g, yield 88%).

Example 9
Synthesis of methyl cyclopropylacrylate

In a 3-necked flask was placed pyridine (342 g, 350 ml, 4.33 mol, 3.23 eq based on the cyclopropanecarboxaldehyde). To the solution was added a small portion of monomethyl malonate (173.6 g, 1,47 mol, 1.1 eq based on the cyclopropanecarboxaldehyde) below 60° C. with stirring. To the reaction solution was added cyclopropanecarboxaldehyde (93.42 g, 100 ml, 1.33 mol). After addition, the reaction mixture was warmed to 80° C. to 90° C. and stirred until the ratio of cyclopropanecarboxaldehyde to methyl cyclopropylacrylate was reduced 5% or less by gas chromatography. The reaction mixture was poured into 3N hydrochloric acid to acidify below pH 1. To the quenched solution was added ethyl acetate and extracted. After separation of aqueous layer, the organic layer was washed with saturated aqueous sodium chloride. The washed organic layer was dried over anhydrous magnesium sulfate, filtered and concentrated to give methyl cyclopropylacrylate (134.2 g, yield 80%).

Example 10
Synthesis of methyl cyclopropylacrylate

To a solution of the mixture of methyl cyclopylacrylate and methyl 3-cyclopropyl-3-methoxypropionate (59.6 g, from Example 1, Example 2, Example 3 or Example 4) in methanol (120 ml) was added potassium carbonate (32.24 g) and stirred for 13 hours at room temperature. After addition of hexane, the upper hexane's layer was separated, filtered and concentrated. The residue was diluted with hexane, filtered, concentrated, and distill (50 mmHg, 101° C. to 102° C.) to give methyl cyclopropylacrylate (23.3 g, yield 62%).

Example 11
Synthesis of cyclopropylacrylic acid

Potassium hydroxide (0.495 kg, purity 86%, 7.59 mol) was dissolved into water (0.768 kg) with stirring at 25±5° C. The mixture of isopropyl cyclopropylacrylate as main product given in example 7 was added to the solution keeping the reaction temperature at 75±5° C. After the addition was complete, the reaction mixture was heated and stirred for 5 hours. After being analyzed the disappearance of the ester by gas chromatography, the reaction mixture was distilled under a slightly reduced pressure (760 to 200 mmHg) azeotropically to remove alcohols with water. Water as the same amount of the removed distillate was added to the residue solution not to concentrate. To the cooled reaction mixture was added dichloromethane (1.855 kg) and 6N hydrochloric acid (1.418 kg). After separation of the organic layer, the organic layer was azeotroped to remove water. After no separation of water from the distillate, the residue solution was cooled to give the dichloromethane solution of cyclopropylacrylic acid (2.65 kg, cyclopropylacrylic acid 0.664 kg as GC internal standard analysis methods, 2 steps yield 82%) with the followed physical data.
$^1$H-NMR spectrum (270 MHz, CDCl$_3$, TMS, ppm) δ: 6.52(dd,J=9.89,14.8 Hz,1H), 5.90(d,J=14.8 Hz,1H) 1.61(m, 1H), 0.99(m,2H), 0.68(m,2H).

Example 12
Synthesis of cyclopropylacrylic acid

To a solution of malonic acid (62.4 g, 0.6 mol) and ammonium acetate (1.5 g) in diisopropyl ether (172 ml) was added pyridine (47.5 g, 0.6 mol) andcyclopropanecarboxaldehyde (35.5 g, 0.5 mol) dropwise. After the addition was complete, the reaction mixture was heated at 70° C. to 75° C. for 2 hours azeotropically to remove water outside. After the reaction was complete, the crude mixture was concentrated to remove diisopropyl ether. To the residue was added 1N hydrochloric acid (650 ml) and extracted with dichloromethane (500 ml) twice. After being washed with saturated aqueous sodium chloride, the extracted layer was concentrated to give cyclopropylacrylic acid (45.6 g, purity 99.1%, yield 80%).

Example 13
Synthesis of cyclopropylacrylic acid

Reaction and separation were conducted in the same manner as in Example 12 except the reaction solvent changed from diisopropyl ether to hexane and reaction time changed from 2 hours to 1.5 hour to give the crude cyclopropylacrylic acid (43.7 g, purity 93.6%, yield 73%).

Comparative Example 1
Synthesis of cyclopropylacrylic acid

To a solution of malonic acid (124.8 g, 1.2 mol) and pyridine (94.9 g, 1.2 mol) was added to cyclopropanecarboxaldehyde (70.0 g, 1.0 mol) and heated at 95° C. to 100° C. for 12 hours. The reaction mixture was poured into 1N hydrochloric acid (1.25l) and extracted with dichloromethane (500 ml) twice. The combined organic layer was washed with saturated aqueous sodium chloride and concentrated to give the crude cyclopropylacrylic acid (70.9 g, purity 93.7%, yield 59.3%).

Example 14
Synthesis of 2,3-dibromo-3-cyclopropylpropionic acid

In a 3-necked flask were placed cyclopropylacrylic acid (5 g, 44.6 mmol) and hexane (50 ml). After cooled below 5° C. in an ice bath, bromine (7.48 g, 46.8 mmol) was added dropwise to suspension under nitrogen atmosphere until a bromine coloration was retained. After the addition was complete, the reaction mixture was warmed to room temperature and stirred for 2 hours. The slurry reaction mixture was filtered to give 2,3-dibromo-3-cyclopropylpropionic acid (8.77 g, yield 72%) as crystal with the followed physical data.

¹H-NMR spectrum (270 MHz, CDCl₃, TMS, ppm) δ: 9.2(bs,1H), 4.66(d,J=10.9 Hz,1H), 3.87(dd,J=9.89,10.9 Hz,1H), 1.2–1.4(m,1H), 1.0–1.15(m,1H), 0.75–0.90(m,2H), 0.4–0.5(m,1H).

Example 15
Synthesis of 2,3-dibromo-3-cyclopropylpropionic acid

In a 3-necked flask were placed cyclopropylacrylic acid (5 g, 44.6 mmol) and dichloromethane (50 ml). After cooled below 5° C. in ice bath, bromine (7.48 g, 46.8 mmol) was added dropwise to the solution under nitrogen atmosphere until a bromine coloration was retained. After the addition was complete, the reaction mixture was warmed to room temperature and stirred for 2 hours. The slurry reaction mixture was filtered to give 2,3-dibromo-3-cyclopropylpropionic acid (7.52 g, yield 62%) as crystal.

Example 16
Synthesis of 2,3-dibromo-3-cyclopropylpropionic acid

In a 3-necked flask were placed cyclopropylacrylic acid (50 g, 446 mmol) and chloroform (300 ml). After cooled below 5° C. in an ice bath, bromine (74.8 g, 468 mmol) was added dropwise to the clear solution under nitrogen atmosphere until a bromine coloration was retained. After the addition was complete, the reaction mixture was warmed to room temperature and stirred for 2 hours. The slurry reaction mixture was filtered to give 2,3-dibromo-3-cyclopropylpropionic acid (62.2 g) as the first crystal crop. The filtrate was concentrated and suspended with hexane (25 ml). The suspension was filtered to give 2,3-dibromo-3-cyclopropylpropionic acid (10.5 g) as the second crystal crop (combined yield of first and second crop 60%).

Example 17
Synthesis of methyl 2,3-dibromo-3-cyclopropyl-2-methoxycarbonylpropionate In a 3-necked flask were placed dimethyl cyclopropylmethylidenemalonate (18.4 g, 0.1 mol) and chloroform (100 ml). After cooled below 5° C. in an ice bath, bromine (17.6 g, 0.11 mol) was added dropwise under nitrogen atmosphere until a bromine coloration was retained. After the addition was complete, the reaction mixture was warmed to room temperature and stirred for 2 hours. The reaction mixture was concentrated to give the crude methyl 2,3-dibromo-3-cyclopropyl-2-methoxycarbonylpropionate (35 g) with the followed physical data.

¹H-NMR spectrum (270 MHz, CDCl₃, TMS, ppm) δ: 3.88(s,3H), 3.86(s,3H), 3.80–3.88(m,1H), 1.61–1.70(m,1H), 0.80–0.95(m,2H), 0.67–0.72(m,1H), 0.44–0.50(m,1H).

Example 18
Synthesis of 2,3-dichloro-3-cyclopropylpropionic acid

In a 3-necked flask were placed cyclopropylacrylic acid (5 g, 44.6 mmol) and dichloromethane (50 ml). After cooled below 5° C. in an ice bath, chlorine gas was passed into the reaction mixture under nitrogen atmosphere until a chlorine coloration was retained. After the reaction mixture was stirred at room temperature for 2 hours, the reaction solution was concentrated to give the crude 2,3-dichloro-3-cyclopropylpropionic acid (8.16 g) with the followed physical data.

¹H-NMR spectrum (270 MHz, CDCl₃, TMS, ppm) δ: 9.2(bs,1H), 4.54(d,J=8.4 Hz,1H), 3.65–3.93(m,1H), 1.25–1.6(m,1H), 0.4–1.0(m,4H).

Example 19
Synthesis of 2-cyclopropylvinyl-1-bromide

In a 3-necked flask were placed 2,3-dibromo-3-cyclopropylpropionic acid (3.74 g, 13.8 mmol). 10%-aqueous potassium carbonate (40.38 g, 2.12 eq based on the 2,3-dibromo-3-cyclopropylpropionic acid, prepared from potassium carbonate 4.03 g and water 36.35 g) was added dropwise slowly. After the addition was complete, the reaction mixture was warmed at 60° C., stirred for 2 hours and cooled to room temperature. After the addition of pentane, the reaction mixture was stirred vigorously and stood for a few minutes. After separation of the aqueous layer, the organic layer was dried over anhydrous sodium sulfate, filtered and concentrated to give 2-cyclopropylvinyl-1-bromide (1.45 g, yield 72%) with the followed physical data.

¹H-NMR spectrum (270 MHz, CDCl₃, TMS, ppm) δ: E-isomer: 6.03(d,J=13.9 Hz,1H), 5.72(dd,J=8.90,13.9 Hz,1H), 1.3–1.5(m,1H), 0.7–0.8(m,2H), 0.3–0.45(m,2H). Z-isomer: 6.04(d,J=6.93 Hz,1H), 5.47(dd,J=6.92,8.90 Hz,1H), 1.75–1.95(m,1H), 0.75–1.00(m,2H), 0.3–0.55(m,2H).

Example 20
Synthesis of 2-cyclopropylvinyl-1-bromide

In a 3-necked flask were placed 2,3-dibromo-3-cyclopropylpropionic acid (30 g, 10 mmol) and pentane (150 ml). To the suspension was added 10%-aqueous potassium carbonate (227.3 g, 165 mmol as potassium carbonate, 1.49 eq based on the 2,3-dibromo-3-cyclopropylpropionic acid) dropwise slowly under reflux. After the addition was complete, the reaction mixture was stirred for 1 hour under reflux, cooled to room temperature, and stood for a few minutes. After separation of the aqueous layer, the organic layer was dried over anhydrous sodium sulfate. The solution was filtered and concentrated to give 2-cyclopropylvinyl-1-bromide (7.57 g, yield 47%, Z-isomer:E-isomer=83:17).

Example 21
Synthesis of 2-cyclopropylvinyl-1-bromide

In a 3-necked flask were placed methanol (150 ml) and potassium carbonate (4.03 g, 29.2 mmol, 2.12 eq based on the 2,3-dibromo-3-cyclopropylpropionic acid). To the suspension was added 2,3-dibromo-3-cyclopropylpropionic acid (3.74 g, 13.75 mmol) at room temperature. After stirred for 4 hours at room temperature, the reaction mixture was poured into water and extracted with pentane. After separation of the aqueous layer, the organic layer was dried over anhydrous sodium sulfate, filtered and concentrated to give 2-cyclopropylvinyl-1-bromide (1.58 g, yield 78%, Z-isomer:E-isomer=83:17).

Example 22
Synthesis of 2-cyclopropylvinyl-1-bromide

In a 3-necked flask were placed methanol (150 ml) 2,3-dibromo-3-cyclopropylpropionic acid (30 g, 110 mmol). To the suspension was added sodium hydrogencarbonate (12.3 g, 116 mmol, 1.05 eq based on the 2,3-dibromo-3-cyclopropylpropionic acid) at 0±5° C. After addition, the reaction mixture was warmed slowly at room temperature (20° C. to 25° C.) and stirred for 7.5 hours. After the reaction was complete, the reaction mixture was poured into water and extracted with dichloromethane. After separation of the organic layer, the organic layer was concentrated under atmosphere pressure and distilled under reduced pressure (65 mmHg, boiling point 62° C.) to give 2-cyclopropylvinyl-1-bromide (12.61 g, yield 78%, purity 95% up, Z-isomer:E-isomer=95:5).

Example 23
Synthesis of 2-cyclopropylvinyl-1-bromide

In a 3-necked flask were placed tert-butanol (150 ml) and potassium hydroxide (7.56 g, purity 86%, 116 mmol, 1.05 eq based on the 2,3-dibromo-3-cyclopropylpropionic acid). To the solution was added 2,3-dibromo-3-cyclopropylpropionic acid (30 g, 110 mmol) at room temperature and stirred for 5 hours. After the reaction was complete, the reaction mixture was poured into water and extracted with hexane. After separation of the aqueous layer, the organic layer was dried over anhydrous sodium sulfate, filtered, concentrated under atmosphere pressure and distilled under reduced pressure (65 mmHg, boiling point 62° C.) to give 2-cyclopropylvinyl-1-bromide was obtained (10.8 g, yield 67%, Z-isomer:E-isomer=83:17).

Example 24
Synthesis of 2-cyclopropylvinyl-1-bromide

In a 3-necked flask were placed methanol (150 ml) and potassium hydroxide (7.56 g, purity 86%, 116 mmol, 1.05 eq based on the 2,3-dibromo-3-cyclopropylpropionic acid). To the solution was added 2,3-dibromo-3-cyclopropylpropionic acid (30 g, 110 mmol) at room temperature and stirred for 7.5 hours. After the reaction was complete, the reaction mixture was poured into water and extracted with hexane. After separation of the aqueous layer, the organic layer was dried over anhydrous sodium sulfate, filtered, concentrated under atmosphere pressure and distilled under reduced pressure (65 mmHg, boiling point 62° C.) to give 2-cyclopropylvinyl-1-bromide (12.45 g, yield 77%, Z-isomer:E-isomer=83:17).

Example 25
Synthesis of 2-cyclopropylvinyl-1-bromide

In a 3-necked flask were placed diisopropyl ether (150 ml) and 2,3-dibromo-3-cyclopropylpropionic acid (30 g, 10 mmol). To the suspension was added triethylamine (11.7 g, 116 mmol, 1.05 eq based on the 2,3-dibromo-3-cyclopropylpropionic acid) at 0±5° C. After the addition was completed, a reaction mixture was warmed slowly to room temperature (20° C. to 25° C.) and stirred for 7.5 hours. After the reaction was complete, the reaction mixture was washed with water (80 g). After separation of the aqueous layer, the organic layer was concentrated under atmosphere pressure to remove diisopropyl ether and distilled under reduced pressure (65 mmHg, boiling point 62° C.) to give 2-cyclopropylvinyl-1-bromide (11.32 g, yield 70%, purity 99% up, Z-isomer:E-isomer=95:5).

Example 26
Synthesis of 2-cyclopropylvinyl-1-bromide

In a 3-necked flask were placed toluene (150 ml) and 2,3-dibromo-3-cyclopropylpropionic acid (30 g, 10 mmol). To the suspension was added triethylamine (11.7 g, 116 mmol, 1.05 eq based on the 2,3-dibromo-3-cyclopropylpropionic acid) at 0±5° C. After the addition was complete, the reaction mixture was warmed slowly to room temperature (20° C. to 25° C.) and stirred for 8 hours. After the reaction was complete, the reaction mixture was washed with water (80 g). After separation of the aqueous layer, the organic layer was concentrated to remove toluene and distilled under reduced pressure (65 mmHg, boiling point 62° C.) to give 2-cyclopropylvinyl-1-bromide (7.92 g, yield 49%, purity 95%, Z-isomer:E-isomer=83:17).

Example 27
Synthesis of 2-cyclopropylvinyl-1-bromide

In a 3-necked flask were placed methanol (150 ml) and 2,3-dibromo-3-cyclopropylpropionic acid (30 g, 10 mmol). To the suspension was added triethylamine (11.7 g, 116 mmol, 1.05 eq based on the 2,3-dibromo-3-cyclopropylpropionic acid) at 0±5° C. After the addition was complete, the reaction mixture was warmed slowly to room temperature (20° C. to 25° C.) and stirred for 7.5 hours. After the reaction was complete, the reaction mixture was added to water and extracted with dichloromethane. After separation of the organic layer (lower phase), the organic layer was concentrated under atmosphere pressure to remove dichloromethane. The residue was distilled under reduced pressure (65 mmHg, boiling point 62° C.) to give 2-cyclopropylvinyl-1-bromide (12.29 g, yield 76%, purity 95%, Z-isomer:E-isomer=83:17).

Example 28
Synthesis of 2-cyclopropylvinyl-1-bromide

In a 3-necked flask were placed dichloromethane (150 ml) and 2,3-dibromo-3-cyclopropylpropionic acid (30 g, 10 mmol). To the suspension was added triethylamine (11.7 g, 116 mmol, 1.05 eq based on the 2,3-dibromo-3-cyclopropylpropionic acid) at 0±5° C. After the addition was complete, the reaction mixture was warmed slowly at room temperature (20° C. to 25° C.) and stirred for 10 hours. After the reaction was complete, the reaction mixture was washed with water (80 g). After separation of the organic layer (lower phase), the organic layer was concentrated under atmosphere pressure to remove dichloromethane. The residue was distilled under reduced pressure (65 mmHg, boiling point 62° C.) to give 2-cyclopropylvinyl-1-bromide (14.71 g, yield 91%, purity 99% up, Z-isomer:E-isomer=95:5).

Example 29
Synthesis of 2-cyclopropylvinyl-1-chloride

In a 3-necked flask were placed dichloromethane (150 ml) and 2,3-dichloro-3-cyclopropylpropionic acid (20.1 g, 10 mmol). To the suspension was added triethylamine (11.7 g, 116 mmol, 1.05 eq based on the 2,3-dichloro-3-cyclopropylpropionic acid) at 0±5° C. After the addition was complete, the reaction mixture was warmed slowly to room temperature (20° C. to 25° C.) and stirred for 10 hours. After the reaction was complete, the reaction mixture was washed with water (80 g). After separation of the organic layer (lower layer), the organic layer was concentrated under atmosphere pressure to remove dichloromethane to give 2-cyclopropylvinyl-1-chloride (5.63 g, yield 50%, Z-isomer:E-isomer=80:20) with the followed physical data.

$^1$H-NMR spectrum (270 MHz, CDCl$_3$, TMS, ppm) δ: E-isomer: 5.97(d,J=12.9 Hz,1H), 5.46(dd,J=8.90,12.9 Hz,1H), 1.3–1.5(m,1H), 0.7–0.8(m,2H), 0.3–0.45(m,2H). Z-isomer: 5,95(d,J=6.93 Hz,1H), 5.14(dd,J=6.93,9.90 Hz,1H), 1.80–1.95(m,1H), 0.75–1.00(m,2H), 0.3–0.55(m, 2H).

Example 30
Synthesis of 2-cyclopropylvinyl-1-bromide

To the dichloromethane solution (217 g) from Example 12 contained cyclopropylacrylic acid (54.39 g) was added bromine (81.41 g, 0.509 mol) dropwise at 0±5° C. under nitrogen atmosphere until a bromine coloration was retained. After the addition was complete, the reaction mixture was stirred at 0±5° C. for 4 hours.

After the reaction was completed by GC analysis, triethylamine (54.54 g, 1.05 eq based on the bromine) was added at 0±5° C. to the suspension. After addition, the reaction mixture was warmed slowly to room temperature (20° C. to 25° C.) and stirred for 10 hours. After the reaction was complete, the reaction mixture was washed with water (80 g). After separation of the organic layer (lower phase), the organic layer was concentrated under atmosphere pressure to remove dichloromethane. The residue was distilled under reduced pressure (65mmHg, boiling point 62° C.) to give 2-cyclopropylvinyl-1-bromide (35.66 g, 2 steps yield 50%, purity 99% up, Z-isomer:E-isomer=95:5).

Example 31
Synthesis of cyclopropylacetylene

In a 3-necked flask were placed 2-cyclopropylvinyl-1-bromide (1.4 g, 9.52 mmol) and dimethyl sulfoxide (10 ml). To the solution was added potassium tert-butoxide (2.15 g, 19.2 mmol, 2.0 eq based on the 2-cyclopropylvinyl-1-bromide) at room temperature under nitrogen atmosphere. After the addition was completed, the reaction mixture was stirred at room temperature for 2 hours and heated to fractionate the crude acetylene. The fraction up to 80° C. was rectified to give cyclopropylacetylene (0.5 g, yield 79%) with the followed physical data.

$^1$H-NMR spectrum (270 MHz, CDCl$_3$, TMS, ppm) δ: 1.76(d,J=1.98 Hz,1H), 1.18–1.30(m,1H), 0.68–1.3(m,4H). $^{13}$C-NMR spectrum (67.5 MHz, CDCl$_3$, TMS, ppm) δ: 63.46, 31.33, 8.19, 4.27.

Example 32
Synthesis of cyclopropylacetylene

In a 3-necked flask were placed 2-cyclopropylvinyl-1-bromide (1.4 g, 9.52 mmol) and heptane (10 ml). To the solution was added potassium tert-butoxide (1.28 g, 11.4 mmol, 1.2 eq based on the 2-cyclopropylvinyl-1-bromide) at room temperature under nitrogen atmosphere. After the addition was complete, the reaction mixture was stirred at room temperature for 2 hours and distilled up to 80° C. to give cyclopropylacetylene (0.28 g, yield 45%).

Example 33
Synthesis of cyclopropylacetylene

In a 3-necked flask were placed 2-cyclopropylvinyl-1-bromide (1.4 g, 9.52 mmol) and toluene (10 ml). To the solution was added potassium tert-butoxide (1.28 g, 11.4 mmol, 1.2 eq based on the 2-cyclopropylvinyl-1-bromide) at room temperature under nitrogen atmosphere. After the addition was complete, the reaction mixture was stirred at room temperature for 2 hours and distilled up to 80° C. to give cyclopropylacetylene (0.43 g, yield 68%).

Example 34
Synthesis of cyclopropylacetylene

In a 3-necked flask were placed 2-cyclopropylvinyl-1-bromide (1.4 g, 9.52 mmol) and tert-amyl alcohol (10 ml). To the solution was added potassium tert-butoxide (1.28 g, 11.4 mmol, 1.2 eq based on the 2-cyclopropylvinyl-1-bromide) at room temperature under nitrogen atmosphere. After the addition was complete, the reaction mixture was stirred at room temperature for 2 hours and distilled up to 80° C. to give cyclopropylacetylene (0.46 g, yield 73%).

Example 35
Synthesis of cyclopropylacetylene

In a 3-necked flask were placed 2-cyclopropylvinyl-1-bromide (1.4 g, 9.52 mmol) and tert-amyl alcohol (10 ml). To the solution was added sodium tert-butoxide (1.10 g, 11.4 mmol, 1.2 eq based on the 2-cyclopropylvinyl-1-bromide) at room temperature under nitrogen atmosphere. After the addition was complete, the reaction mixture was stirred at room temperature for 2 hours and distilled up to 80° C. to give cyclopropylacetylene (0.37 g, yield 59%).

Example 36
Synthesis of cyclopropylacetylene

In a 3-necked flask was placed sec-butanol (1523 g). Potassium hydroxide (296 g, purity 86%, 4.54 mol, 1.2 eq based on the 2-cyclopropylvinyl-1-bromide) was added in the flask and dissolved with stirring at 70° C. to 80° C. under nitrogen atmosphere. To the solution was added 2-cyclopropylvinyl-1-bromide (555 g, 3.77 mol) at 45° C. to 50° C. After the addition was complete, the reaction mixture was heated gently to 85° C. to 95° C. to fractionate the crude acetylene up to 95° C. After separation of the lower layer (water) from the fraction, the upper layer's moisture was removed by azeotrope. The dried residue was rectified to give cyclopropylacetylene (211.8 g, boiling point 52.5° C. to 52.7° C., purity 99.8%, yield 85%).

Example 37
Synthesis of cyclopropylacetylene

In a 3-necked flask was placed tert-amyl alcohol (1.5 kg). Potassium hydroxide (296 g, purity 86%, 4.54 mol, 1.2 eq based on the 2-cyclopropylvinyl-1-bromide) was added in the flask and dissolved with stirring at 70° C. to 80° C. under nitrogen atmosphere. To the solution was added 2-cyclopropylvinyl-1-bromide (555 g, 3.77 mol) at 45° C. to 50° C. After the addition was complete, the reaction mixture was heated gently to 85° C. to 95° C. to fractionate the crude acetylene up to 95° C. After separation of the lower layer from the fraction, the upper layer's moisture was removed by azeotrope. The dried residue was rectified to give cyclopropylacetylene (187 g, boiling point 52° C. to 53° C., purity 98%, yield 75%).

Example 38
Synthesis of cyclopropylacetylene

In a 3-necked flask were placed heptane (150 ml) and 2,3-dibromo-3-cyclopropylpropionic acid (30 g, 110 mmol). Potassium tert-butoxide (27.2 g, 242 mmol) was added to the mixture at 0±5° C. After the addition was complete, the reaction mixture was warmed to room temperature (20° C. to 25° C.) and stirred for 10 hours. The reaction mixture was distilled at 85° C. to 95° C. to fractionate the crude the acetylene up to 95° C. After separation of the lower layer from the fraction. The upper layer's moisture was removed by azeotrope. The dried residue was rectified to give cyclopropylacetylene (3.65 g, boiling point 52° C. to 53° C., purity 90%, 2 steps yield 50%).

Example 39
Synthesis of cyclopropylacetylene

In a 3-necked flask were placed dichloromethane (245 ml) and 2,3-dibromo-3-cyclopropylpropionic acid (132 g, 485 mmol). Triethylamine (54.5 g, 539 mmol) was added at 0±5° C. to the suspension. After the addition was complete, the reaction mixture was warmed slowly to room temperature (20° C. to 25° C.) and stirred for 10 hours. After the reaction was complete, the reaction mixture was washed with water (80 g). The lower organic layer was concentrated under atmosphere pressure to remove dichloromethane.

To the residue was added a solution of potassium hydroxide (38.0 g, purity 86%, 677 mol) in sec-butanol (200 ml) and heated at 85° C. to 95° C. to fractionate the crude the acetylene up to 95° C. After separation of the lower layer from the fraction, the upper layer's moisture was removed by azeotrope. The dried residue was rectified to give cyclopropylacetylene (14.3 g, boiling point 52° C. to 53° C., purity 90%, 2 steps yield 40%).

Example 40
Synthesis of cyclopropylacetylene

To a solution of cyclopropylacrylic acid (54.39 g, 0.485 mol) in dichloromethane (244.76 g) was added bromine (81.41 g, 0.509 mol) dropwise at 0±5° C. under nitrogen atmosphere until a bromine coloration was retained. After the addition was completed, the reaction mixture was stirred at 0±5° C. for 4 hours.

After the reaction was completed by GC analysis, triethylamine (54.54 g, 1.05 eq based on the bromine) was added at 0±5° C. to the suspension. After the addition was complete, the reaction mixture was warmed slowly to room temperature (20° C. to 25° C.) and stirred for 10 hours. After the reaction was complete, the reaction mixture was washed with water (80 g). After separation of the organic layer (lower phase), the organic layer was concentrated under atmosphere pressure to remove dichloromethane.

To the residue was added a solution of potassium hydroxide (37.98 g, purity 86%, 0.582 mol) in sec-butanol (200 g) and heated at 85° C. to 95° C. to fractionate the crude acetylene up to 95° C. After separation of the lower layer from the fraction, the upper layer's moisture was removed by azeotrope. The dried residue was rectified to give cyclopropylacetylene (9.62 g, boiling point 52° C. to 53° C., purity 90%, 2 steps yield 30%).

What is claimed is:

1. A process for the preparation of a cyclopropylacetylene derivative represented by the following formula (III):

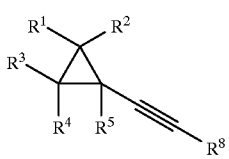

(III)

wherein $R^1$, $R^2$, $R^3$, $R^4$ and $R^5$ each represents a hydrogen atom or an alkyl group which may have a substituent, and $R^8$ represents a hydrogen atom, an alkyl group which may have a substituent, a carboxyl group or a protected carboxyl group, which comprises reacting a cyclopropylacrylic acid derivative represented by the following formula (I):

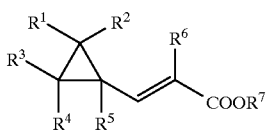

(I)

wherein $R^1$, $R^2$, $R^3$, $R^4$ and $R^5$ have the same meanings as defined above, $R^6$ represents a hydrogen atom, an alkyl group which may have a substituent, a carboxyl group or a protected carboxyl group, and $R^7$ represents a hydrogen atom or a protecting group for a carboxyl group, with a halogenating agent to obtain a halogenocyclopropylpropionic acid derivative represented by the following formula (II):

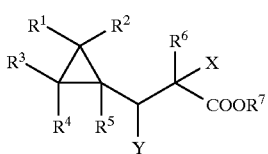

(II)

wherein $R^1$, $R^2$, $R^3$, $R^4$, $R^5$, $R^6$ and $R^7$ have the same meanings as defined above, and X and Y each represents a halogen atom, and reacting the halogenocyclopropylpropionic acid derivative with a base.

2. A process for the preparation of a cyclopropylacetylene derivative represented by the following formula (III):

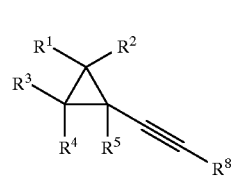

(III)

wherein $R^1$, $R^2$, $R^3$, $R^4$ and $R^5$ each represents a hydrogen atom or an alkyl group which may have a substituent, and $R^8$ represents a hydrogen atom, an alkyl group which may have a substituent, a carboxyl group or a protected carboxyl group, which comprises reacting a halogenocyclopropylpropionic acid derivative represented by the following formula (II):

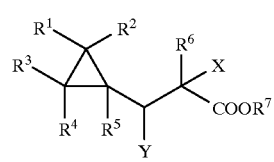

(II)

wherein $R^1$, $R^2$, $R^3$, $R^4$ and $R^5$ have the same meanings as defined above, $R^6$ represents a hydrogen atom, an alkyl group which may have a substituent, a carboxyl group or a protected carboxyl group, $R^7$ represents a hydrogen atom or a protecting group for a carboxyl group, and X and Y each represents a halogen atom, with a base.

3. A process for the preparation of a cyclopropylacetylene derivative represented by the following formula (III):

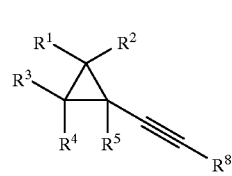

(III)

wherein $R^1$, $R^2$, $R^3$, $R^4$ and $R^5$ each represents a hydrogen atom or an alkyl group which may have a substituent, and $R^8$ represents a hydrogen atom, an alkyl group which may have a substituent, a carboxyl group or a protected carboxyl group, which comprises reacting a halogenocyclopropylpropionic acid derivative represented by the following formula (II):

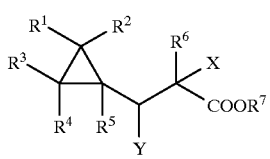
(II)

wherein $R^1$, $R^2$, $R^3$, $R^4$ and $R^5$ have the same meanings as defined above, $R^6$ represents a hydrogen atom, an alkyl group which may have a substituent, a carboxyl group or a protected carboxyl group, $R^7$ represents a hydrogen atom or a protecting group for a carboxyl group, and X and Y each represents a halogen atom, with a base to obtain a cyclopropylvinyl derivative represented by the following formula (IV):

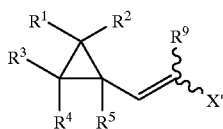
(IV)

wherein $R^1$, $R^2$, $R^3$, $R^4$, $R^5$ and X have the same meanings as defined above, and $R^9$ represents a hydrogen atom, an alkyl group which may have a substituent, a carboxyl group or a protected carboxyl group, and reacting the cyclopropylvinyl derivative with a base.

4. A process for the preparation of a cyclopropylacetylene derivative represented by the following formula (III):

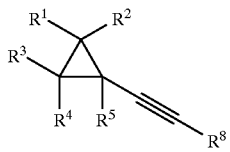
(III)

wherein $R^1$, $R^2$, $R^3$, $R^4$ and $R^5$ each represents a hydrogen atom or an alkyl group which may have a substituent, and $R^8$ represents a hydrogen atom, an alkyl group which may have a substituent, a carboxyl group or a protected carboxyl group, which comprises reacting a cyclopropylvinyl derivative represented by the following formula (IV):

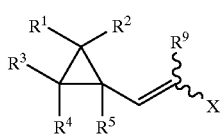
(IV)

wherein $R^1$, $R^2$, $R^3$, $R^4$ and $R^5$ have the same meanings as defined above, $R^9$ represents a hydrogen atom, an alkyl group which may have a substituent, a carboxyl group or a protected carboxyl group, and X represents a halogen atom, with a base.

5. A process for the preparation of a cyclopropylvinyl derivative represented by the following formula (IV):

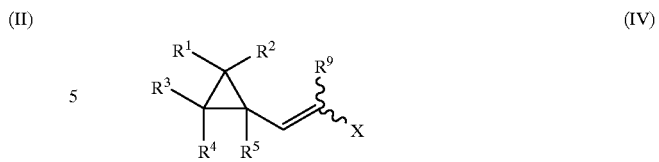
(IV)

wherein $R^1$, $R^2$, $R^3$, $R^4$ and $R^5$ each represents a hydrogen atom or an alkyl group which may have a substituent, $R^9$ represents a hydrogen atom, an alkyl group which may have a substituent, a carboxyl group or a protected carboxyl group, and X represents a halogen atom, which comprises reacting a halogenocyclopropylpropionic acid derivative represented by the following formula (II):

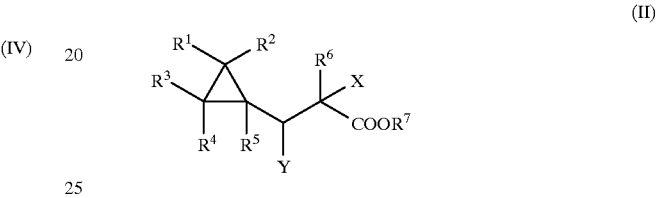
(II)

wherein $R^1$, $R^2$, $R^3$, $R^4$, $R^5$ and X have the same meanings as defined above, $R^6$ represents a hydrogen atom, an alkyl group which may have a substituent, a carboxyl group or a protected carboxyl group, $R^7$ represents a hydrogen atom or a protecting group for a carboxyl group, and Y represents a halogen atom, with a base.

6. A process for the preparation of a cyclopropylvinyl derivative represented by the following formula (IV):

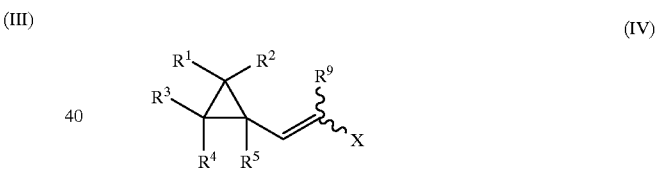
(IV)

wherein $R^1$, $R^2$, $R^3$, $R^4$ and $R^5$ each represents a hydrogen atom or an alkyl group which may have a substituent, $R^9$ represents a hydrogen atom, an alkyl group which may have a substituent, a carboxyl group or a protected carboxyl group, and X represents a halogen atom, which comprises reacting a cyclopropylacrylic acid derivative represented by the following formula (I):

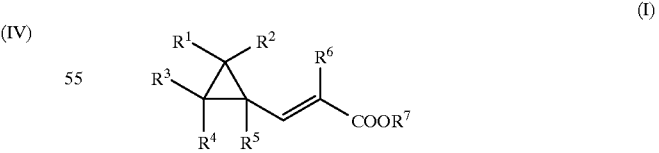
(I)

wherein $R^1$, $R^2$, $R^3$, $R^4$ and $R^5$ have the same meanings as defined above, $R^6$ represents a hydrogen atom, an alkyl group which may have a substituent, a carboxyl group or a protected carboxyl group, and $R^7$ represents a hydrogen atom or a protecting group for a carboxyl group, with a halogenating agent and a base.

7. A cyclopropylvinyl derivative represented by the following formula (IV-I):

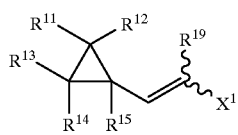

wherein $R^{11}$, $R^{12}$, $R^{13}$, $R^{14}$ and $R^{15}$ each represents a hydrogen atom or an alkyl group which may be substituted with a hydroxyl group, an alkoxyl group or an aryl group, $R^{19}$ represents a hydrogen atom, an alkyl group which may have a substituent, a carboxyl group or a protected carboxyl group, and $X^1$ represents a halogen atom, with the proviso that both:

(a) when all of $R^{11}$, $R^{12}$, $R^{13}$, $R^{14}$, $R^{15}$ and $R^{19}$ are hydrogen, $X^1$ is other than fluorine, and (b) when $R^{15}$ is hydrogen or methyl, and $R^{19}$ is —$CO_2CH_3$, $X^1$ is other than iodine.

8. A cyclopropylvinyl derivative represented by the following formula (IV-I):

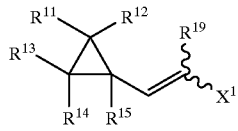

wherein $R^{11}$, $R^{12}$, $R^{13}$, $R^{14}$ and $R^{15}$ each represents a hydrogen atom or an alkyl group which may be substituted with a hydroxyl group, an alkoxyl group or an aryl group, $R^{19}$ represents a hydrogen atom, an alkyl group which may have a substituent, a carboxyl group or a protected carboxyl group, and $X^1$ represents a chlorine or bromine atom.

9. A halogenocyclopropylpropionic acid derivative represented by the following formula (II):

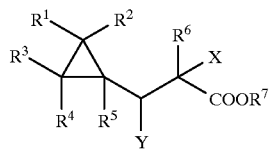

wherein $R^1$, $R^2$, $R^3$, $R^4$ and $R^5$ each represents a hydrogen atom or an alkyl group which may have a substittent, $R^6$ represents a hydrogen atom, an alkyl group which may have a substituent, a carboxyl group or a protected carboxyl group, $R^7$ represents a hydrogen atom or a protecting group for a carboxyl group, and X and Y each represents a halogen atom.

10. A process for the preparation of a halogenocyclopropylpropionic acid derivative represented by the following formula (II):

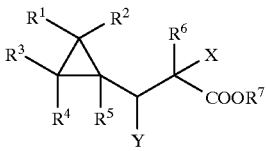

wherein $R^1$, $R^2$, $R^3$, $R^4$ and $R^5$ each represents a hydrogen atom or an alkyl group which may have a substituent, $R^6$ represents a hydrogen atom, an alkyl group which may have a substituent, a carboxyl group or a protected carboxyl group, $R^7$ represents a hydrogen atom or a protecting group for a carboxyl group, and X and Y each represents a halogen atom, which comprises reacting a cyclopropylacrylic acid derivative represented by the following formula (I):

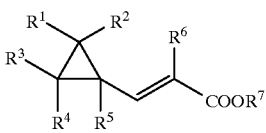

wherein $R^1$, $R^2$, $R^3$, $R^4$, $R^5$, $R^6$ and $R^7$ have the same meanings as defined above, with a halogenating agent.

11. A process for the preparation of a cyclopropylacrylic acid derivative represented by the following formula (I):

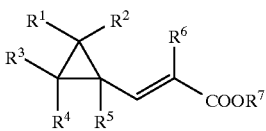

wherein $R^1$, $R^2$, $R^3$, $R^4$ and $R^5$ each represents a hydrogen atom or an alkyl group which may have a substituent, $R^6$ represents a hydrogen atom, an alkyl group which may have a substituent, a carboxyl group or a protected carboxyl group, and $R^7$ represents a hydrogen atom or a protecting group for a carboxyl group, which comprises reacting a cyclopropanecarboxyaldehyde derivative represented by the following formula (V):

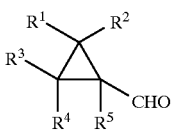

wherein $R^1$, $R^2$, $R^3$, $R^4$ and $R^5$ have the same meanings as defined above, with an ester in the presence of a base selected from the group consisting of amines, carbonates, metal hydroxides and metal alkoxides.

12. A process for the preparation of a cyclopropylacrylic acid derivative represented by the following formula (I):

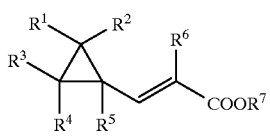

(I)

wherein $R^1$, $R^2$, $R^3$, $R^4$ and $R^5$ each represents a hydrogen atom or an alkyl group which may have a substituent, $R^6$ represents a hydrogen atom, an alkyl group which may have a substituent, a carboxyl group or a protected carboxyl group, and $R^7$ represents a hydrogen atom or a protecting group for a carboxyl group, which comprises reacting a cyclopropanecarboxaldehyde derivative represented by the following formula (V):

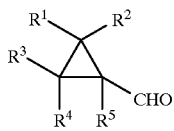

(V)

wherein $R^1$, $R^2$, $R^3$, $R^4$ and $R^5$ have the same meanings as defined above, with an ester in the presence of a base to obtain a cyclopropylpropionic acid derivative represented by the following formula (VI):

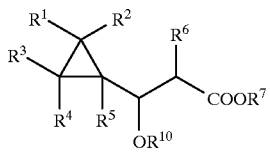

(VI)

wherein $R^1$, $R^2$, $R^3$, $R^4$, $R^5$, $R^6$ and $R^7$ have the same meanings as defined above, and $R^{10}$ represents a hydrogen atom or an alkyl group which may have a substituent, and subjecting the cyclopropylpropionic acid derivative to an elimination reaction in the presence of a base.

13. A cyclopropylpropionic acid derivative represented by the formula (VI-1):

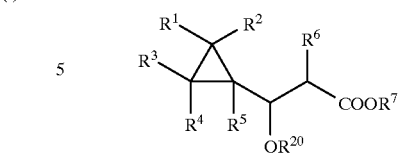

(VI-1)

wherein $R^1$, $R^2$, $R^3$, $R^4$ and $R^5$ each represents a hydrogen atom or an alkyl group which may have a substituent, $R^6$ represents a hydrogen atom, an alkyl group which may have a substituent, a carboxyl group or a protected carboxyl group, $R^7$ represents a hydrogen atom or a protecting group for a carboxyl group, and $R^{20}$ represents an alkyl group which may have a substituent.

14. A process for the preparation of cyclopropylacrylic acid derivative represented by the following formula (I-1):

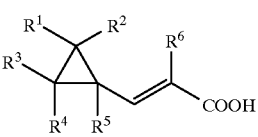

(I-1)

wherein $R^1$, $R^2$, $R^3$, $R^4$ and $R^5$ each represents a hydrogen atom or an alkyl group which may have a substituent, and $R^6$ represents a hydrogen atom, an alkyl group which may have a substituent, a carboxyl group or a protected carboxyl group, which comprises reacting a cyclopropanecarboxaldehyde derivative represented by the following formula (V):

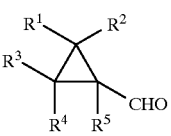

(V)

wherein $R^1$, $R^2$, $R^3$, $R^4$ and $R^5$ have the same meanings as defined above, with malonic acid in the presence of a base while a produced water is removed outside the reaction system.

* * * * *